(12) United States Patent
Marar (10) Patent No.: US 7,502,444 B2
(45) Date of Patent: Mar. 10, 2009

(54) X-RAY APPARATUS HAVING PORTABLE VISUAL INDICATOR

(75) Inventor: Rajeev R. Marar, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/753,777

(22) Filed: May 25, 2007

(65) Prior Publication Data

US 2008/0292056 A1 Nov. 27, 2008

(51) Int. Cl.
*H05G 1/64* (2006.01)
(52) U.S. Cl. .......................... 378/98; 378/101; 378/117
(58) Field of Classification Search .................. 378/91, 378/98, 98.2, 98.3, 98.5, 101, 102, 114–118, 378/204
See application file for complete search history.

(56) References Cited

U.S. PATENT DOCUMENTS 4,170,735 A * 10/1979 Codina et al. ................. 378/96
5,848,126 A * 12/1998 Fujita et al. .................. 378/195
6,285,742 B1 * 9/2001 Haumann et al. ........... 378/116

* cited by examiner

*Primary Examiner*—Jurie Yun
(74) *Attorney, Agent, or Firm*—Peter Vogel, Esq.; William Baxter, Esq.; Michael G. Smith, Esq.

(57) ABSTRACT

In embodiments, x-ray apparatus for imaging a subject, the x-ray apparatus having a base assembly and an x-ray source supported by the base assembly, the x-ray source being operable for generating x-ray energy, the x-ray apparatus having a control system for controlling operation of the x-ray source, the x-ray apparatus including: a detector for detecting a monitored condition, the detector generating detector output; the control system receiving the detector output; and the control system including a portable visual indicator independent of the base assembly and portable in relation thereto, the portable visual indicator displaying a state of the monitored condition.

20 Claims, 5 Drawing Sheets

X-RAY APPARATUS HAVING PORTABLE VISUAL INDICATOR

FIELD OF THE INVENTION

The present disclosure relates to improved apparatus for x-ray imaging.

BACKGROUND OF THE INVENTION

The present disclosure relates generally to apparatus for x-ray imaging. More particularly, embodiments of the present disclosure relate to x-ray apparatus for fluoroscopic medical imaging. X-ray apparatus includes an x-ray source supported by a base assembly. The x-ray source, typically an x-ray tube, is selectively operable for generating x-ray energy for imaging a subject. X-ray apparatus includes a receptor for receiving x-ray energy to create an exposure image. An elongated arm extends from the base assembly and supports the x-ray source in relation to the subject being imaged. The x-ray apparatus also includes a control system connected for selectively controlling operation of the x-ray source and receptor. The control system includes a system host display supported on the base assembly for visual display of system information and patient information to an operator. The control system includes an exposure prep and hold switch which is manually engaged by the operator for selectively operating the x-ray source to generate x-ray energy for creating an exposure.

The system host display on the base assembly displays information to the operator when the operator is located within visual range of the system host display in order to view information displayed thereon. The displayed information can include patient information, system information such as operating parameters, and detected conditions of the x-ray apparatus, patient and surrounding environment. As further discussed herein, a number of conditions are monitored and must meet established parameters in order for the control system to enable operation of the x-ray source, upon two step operation of the exposure prep and hold switch by the operator, and thus generate x-ray energy for creating an exposure.

The control system includes numerous detectors for detecting selected conditions of the x-ray apparatus, the subject, and the operating environment. When the x-ray apparatus is in "acquire" mode for generating an exposure, the detectors monitor the numerous conditions which can enable or inhibit operation of the x-ray apparatus for generating an exposure. The total number of monitored conditions can number in the hundreds or greater. Examples of the monitored conditions can include, among others, temperatures, positioning of the receptor, positioning of the subject, and the presence of obstructions.

Monitored conditions which inhibit operation of the x-ray apparatus for generating an exposure at any particular time are said to be "active" inhibit conditions. The control system is structured such that any active inhibit condition disables the prep and hold switch from triggering the x-ray source to fire or operate. Thus, all active inhibit conditions must be corrected by the operator before the exposure prep and hold switch is enabled. All active inhibit conditions are indicated on the system host display mounted on the base assembly. The operator must view all active inhibit conditions displayed on the system host display, in order to determine the corrections which must be made in order to enable the exposure prep and hold switch. Correction of every active inhibit condition can require the operator to repeatedly return to the base assembly to view remaining active inhibit conditions and repeatedly move about correcting such conditions. When every active inhibit condition is corrected, the exposure prep and hold switch is enabled. When the exposure prep and hold switch is enabled, operation of the exposure prep and hold switch by the operator triggers the x-ray source to fire and generate x-ray energy for the desired exposure.

Repeatedly returning to the base assembly to view the system host display and determine active inhibit conditions requires the operator to leave the unattended subject waiting for an extended period. Unattended waiting increases chances that the position of the subject in relation to the receptor will shift to an incorrect position for the imaging exposure. Extended waiting also contributes to fatigue of the subject. Repeatedly returning to the base assembly to view the system host display and determine active inhibit conditions, and then moving to correct each condition, requires time, effort and extensive foot travel of the operator. Time required for determining and correcting active inhibit conditions increases the effective cycle period of the x-ray apparatus above the nominal cycle period and cumulatively increases the overall period and expense required to generate a series of exposures.

For the reasons stated above, and for other reasons stated below which will become apparent to those skilled in the art upon reading and understanding the present specification, there is a need in the art for improved x-ray apparatus having a portable visual indicator of information.

BRIEF DESCRIPTION OF THE INVENTION

The above-mentioned shortcomings, disadvantages and problems are addressed herein, which will be understood by reading and studying the following specification.

In one aspect, embodiments provide x-ray apparatus for imaging a subject, the x-ray apparatus having a base assembly and an x-ray source supported by the base assembly, the x-ray source being operable for generating x-ray energy, the x-ray apparatus having a control system for controlling operation of the x-ray source. The x-ray apparatus includes a detector for detecting a respective monitored condition and generating detector output. The control system receives the detector output and includes a portable visual indicator independent of the base assembly and portable in relation thereto, and the portable visual indicator displays a state of the monitored condition.

In another aspect, embodiments provide x-ray apparatus for imaging a subject, the x-ray apparatus having a base assembly and an x-ray source supported by the base assembly, the x-ray source being operable for generating x-ray energy, and the x-ray apparatus having a control system for controlling operation of the x-ray source. The x-ray apparatus includes the control system having a portable visual indicator carried by an operator and portable in relation to the base assembly. The portable visual indicator has a portable visual display. The control system includes a visual representation of at least one condition displayed on the portable visual display.

In another aspect, embodiments provide x-ray apparatus for imaging a subject, the x-ray apparatus having a base assembly and an x-ray source supported by the base assembly, the x-ray source being operable for generating x-ray energy, the x-ray apparatus having a control system for controlling operation of the x-ray source, the x-ray apparatus including a plurality of detectors, each detector being operable to monitor a respective condition. The x-ray apparatus includes the control system having a portable visual indicator carried by an operator, the portable visual indicator having a portable visual display. The control system includes a plurality of visual representations, each visual representation corresponding to a respective condition. The portable visual indicator includes at least one of the visual representations displayed on the portable visual display, the at least one of the visual representations indicating a state of the respective at least one condition. The control system includes a control for selectively displaying different visual representations from among the plurality of visual representations.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
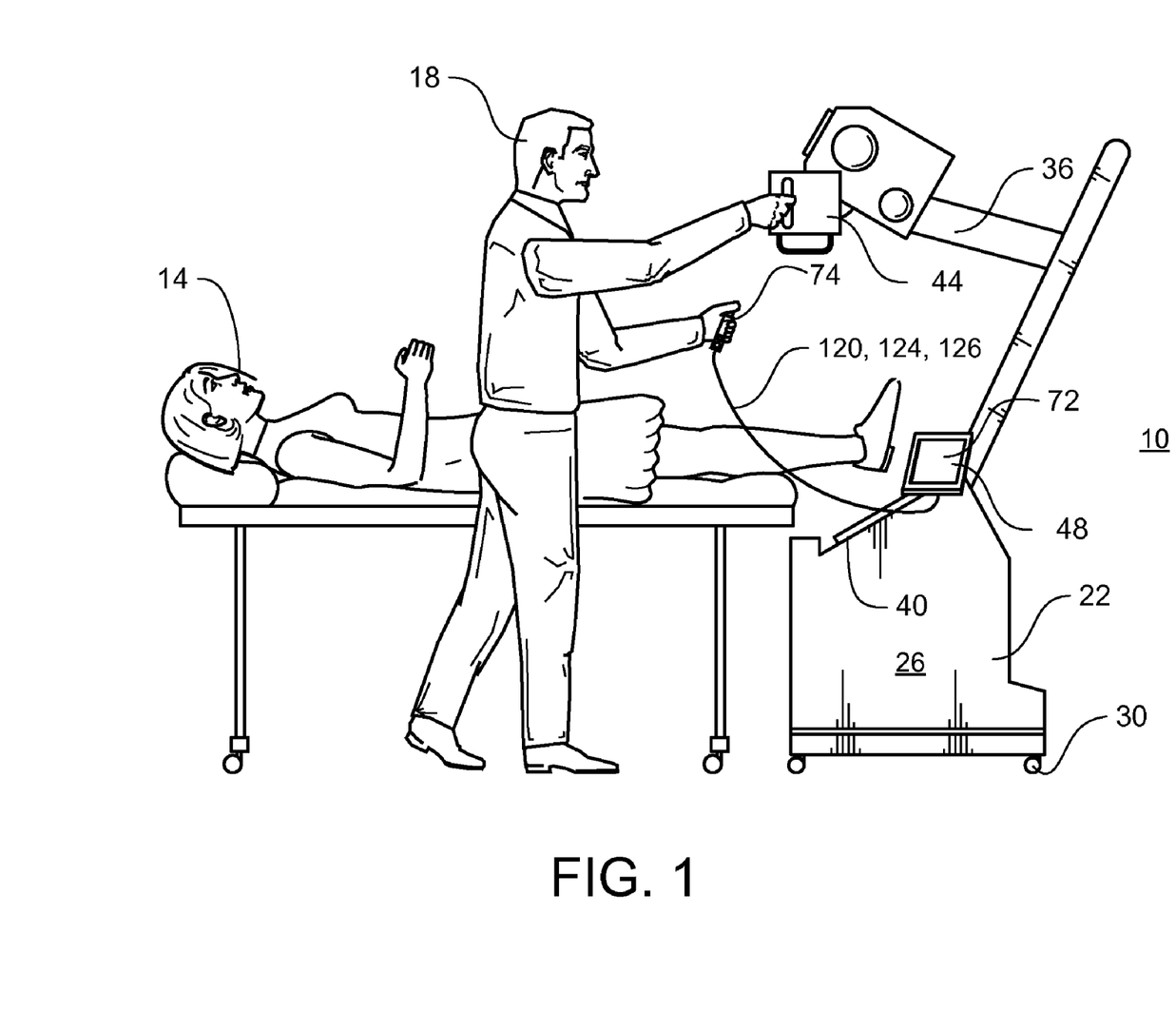
FIG. 1 is a side view of an x-ray apparatus according to a first embodiment.

Illustrated in FIG. 1 is an x-ray apparatus 10 according to a first embodiment. One specific example of an x-ray apparatus 10 according to an embodiment is a high performance computed tomography (CT) x-ray imaging apparatus (not shown) which accommodates a human subject for medical imaging. In other embodiments (not shown), x-ray apparatus 10 according to the present disclosure can be adapted for imaging luggage, containers or other material or subjects, such as for airline, other transportation, shipping, or general security screening. In the specific embodiment illustrated in FIG. 1, x-ray apparatus 10 is adapted for imaging a human subject 14. In the specific arrangement shown in FIG. 1, human subject 14 is positioned for imaging a lower leg thereof. An operator 18 controls operation of the x-ray apparatus 10, as further described herein.

X-ray apparatus 10 includes base assembly 22. In the specific embodiment illustrated in FIG. 1, base assembly 22 includes body 26 and a set of wheels 30 adapted to support body 26 for rolling movement on a floor between different locations in a medical facility. It is to be understood that, in other embodiments (not shown), the base assembly 22 can be situated in a fixed location. Although base assembly 22 is adapted to be supported on floor 32, in other embodiments (not shown) base assembly 22 can be supported in any suitable manner, such as by being mounted on a wall. Base assembly 22 includes movable arm 36 supported by body 26. Movable arm 36 is selectively movable for pivotable movement in relation to subject 14 between desired static positions for imaging desired areas of subject 14. In the specific position illustrated in FIG. 1, arm 36 is positioned for imaging the lower leg area of subject 14. In the specific embodiment illustrated, arm 36 is a folding arm having upper and lower portions connected by an elbow joint for relative folding movement. It is to be understood that, in other embodiments (not shown), arm 36 can be of any suitable construction such as, for example, a "C-arm".

X-ray apparatus 10 includes x-ray source 40 supported by base assembly 22. In the specific embodiment illustrated in FIG. 1, x-ray source 40 is supported by body 26 of base assembly 22. X-ray source 40 is connected to a power source (not shown) and is selectively operable to generate x-ray energy for exposing subject 14.

X-ray apparatus 10 includes receptor 44 supported by base assembly 22 in spaced relation to x-ray source 40. In the specific embodiment illustrated in FIG. 1, receptor 44 is supported by arm 36 of base assembly 22. Arm 36 is movable relative to body 26 for selectively positioning x-ray receptor 44 in relation to an area of subject 14 to be imaged. In the specific arrangement illustrated in FIG. 1, x-ray receptor 44 is disposed in relation to the lower leg of subject 14 for imaging the same. In other embodiments (not shown), receptor 44 can be supported by a movable arm, such as a C-arm, of the base assembly. X-ray receptor 44 is selectively operable to receive x-ray energy generated by x-ray source 40 for creating an exposure image of subject 14.

X-ray apparatus 10 includes control system 48 operably connected for selectively controlling operation of x-ray source 40 and receptor 44. Control system 48 includes suitable circuitry (not shown) operably connected to x-ray source 40 for selectively controlling and operating x-ray source 40 to generate x-ray energy for creating an exposure. Control system 48 also includes suitable circuitry (not shown) connected to receptor 44 for selectively controlling and operating receptor 44 to receive x-ray energy for creating an exposure image of subject 14. It will be appreciated by those skilled in the art that control system 48 can include any combination of elements arranged to control and operate at least one of x-ray source 40 and receptor 44. It will also be appreciated by those skilled in the art that control system 48 can include, in some embodiments, combinations of control system elements arranged to control and operate other functional elements (not shown) such as, for example, lighting and heart rate monitors, in addition to x-ray source 40 and receptor 44. In one embodiment, control system 48 includes at least one processor (not shown) connected to execute at least one executable software application (not shown) stored in memory or storage (not shown) and connected for selectively controlling and operating x-ray source 40 and receptor 44. It will be appreciated by those skilled in the art that control system 48 can be operated in different modes for accomplishing different functions of x-ray apparatus 10. In the specific embodiment illustrated, control system 48 can be operated in "Acquire mode" for operating x-ray source 40 to generate x-ray energy for exposing subject 14 and for operating receptor 44 to create or "acquire" an exposure image thereof. In the specific embodiment illustrated, control system 48 can be operated in modes different from the "Acquire Mode", such as, for example, "Programming Mode" for acquiring data about the procedure, parameters, and subject 14.

Figure 2:
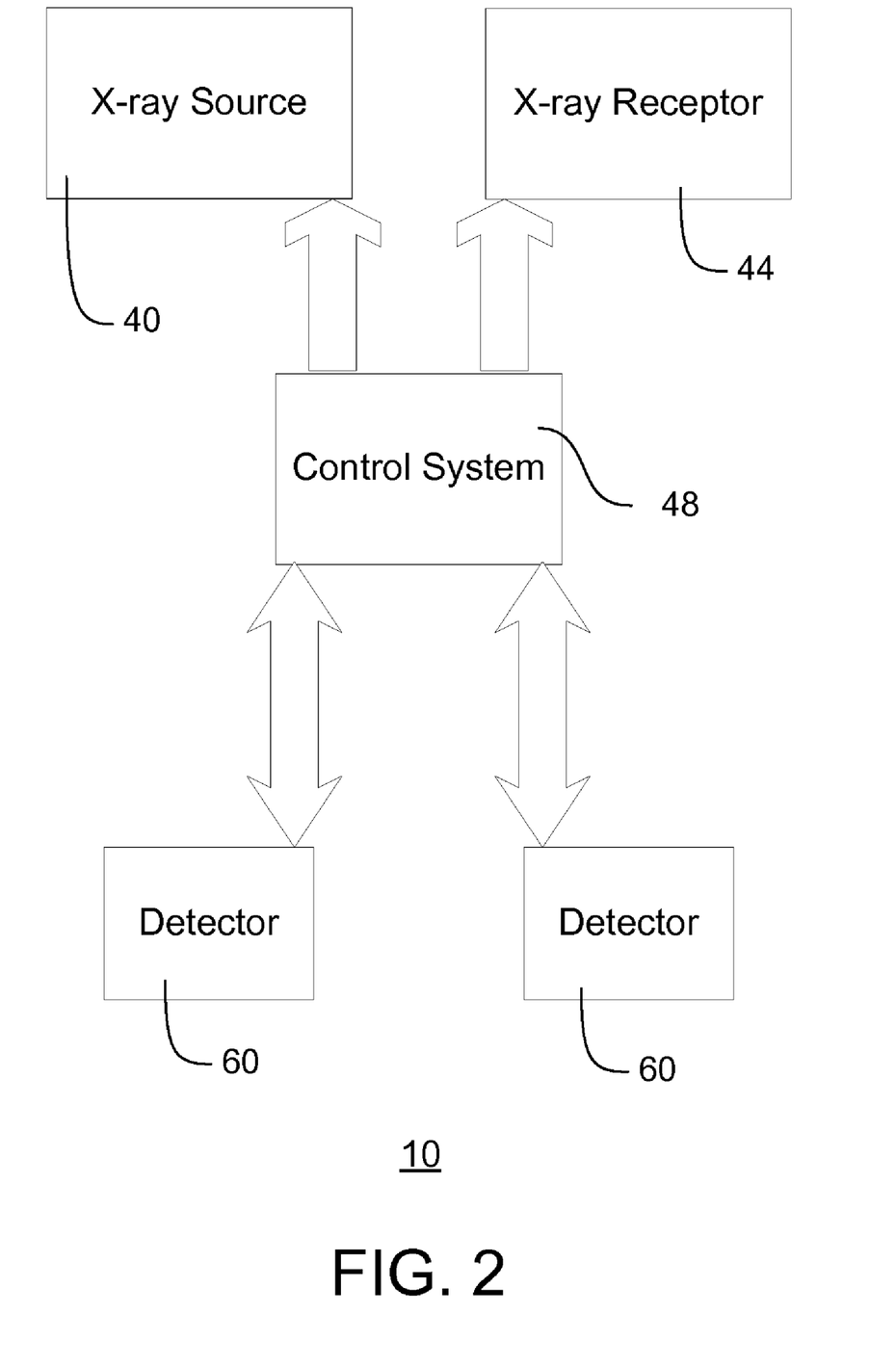
FIG. 2 is a partial block diagram of x-ray apparatus shown in FIG. 1.

FIG. 2 is a partial block diagram of apparatus 10. As best shown in FIG. 2, apparatus 10 includes a plurality of detectors 60 each in communication with control system 48. Detectors 60 are operable to monitor conditions necessary for operation of x-ray source 40 and receptor 44, and are connected to control system 48 to provide output thereto. The monitored conditions necessary for operation of x-ray source 40 and receptor 44 are, more specifically, referred to as "Inhibit Conditions" because, when the Control System is in the Acquire Mode, each monitored condition will inhibit or prevent operation of the x-ray source 40 to generate an exposure when the status of the respective monitored condition falls outside established parameters for safe and effective operation of the x-ray apparatus 10. The monitored conditions can include conditions of the x-ray apparatus 10 such as, for example, temperature of the x-ray source 40 and the status of receptor 44 for receiving x-ray energy to create an exposure. The monitored conditions can include conditions of the subject 14 such as, for example, position of the subject 14 in relation to receptor 44 and the pulse rate of subject 14. The monitored conditions can include conditions of the surrounding environment such as, for example, proximity of metal objects to the x-ray source 40 and other environmental conditions impacting safety. In an embodiment, apparatus 10 includes at least one detector 60 for monitoring a respective condition of at least one of apparatus 10, subject 14 and the surrounding environment. In the specific embodiment illustrated, control system 48 includes a plurality of detectors 60 each connected to monitor a condition of a respective one of x-ray apparatus 10, subject 14 and the surrounding environment. In one embodiment, a detector 60 is connected to monitor a condition selected from among the following: exposure hold condition, system parameters, conditions inhibiting activity, system status conditions, technique settings, and patient information.

Each detector 60 generates a respective detector output associated with the respective monitored condition at a given time. Each detector 60 is connected to provide such output to control system 48 for monitoring the respective condition. Based upon output from a detector 60, control system 48 provides an indicated state of the respective monitored condition. In the specific embodiment illustrated, the indicated state of each monitored condition is indicated either as "Inhibit Status" or "Acceptable Status". "Inhibit Status" means that the state of the monitored condition presently falls outside established parameters for safe and effective operation of the x-ray source 40 to generate x-ray energy for creating an exposure. Thus, when the indicated state of any monitored condition is "Inhibit Status", and the control system 48 is in "Acquire Mode", control system 48 disables or "inhibits" operation of x-ray source 40 to generate x-ray energy for creating an exposure. "Acceptable Status" means that the monitored state presently falls within established parameters for safe and effective operation of the x-ray source 40 to generate x-ray energy for creating an exposure. When the indicated state of any monitored condition is "Acceptable Status", and the control system 48 is in "Acquire Mode", control system 48 does not disable operation of x-ray source 40 to generate x-ray energy for creating an exposure. In the specific embodiment illustrated, each monitored condition must be in a state of "Acceptable Status" in order for control system 48 to enable operation of x-ray source 40 to generate x-ray energy for creating an exposure. Thus, in the illustrated embodiment, each monitored condition in a state of "Inhibit Status" must be changed to "Acceptable Status" before x-ray source 40 can be enabled to operate for generating x-ray energy to create an exposure. When all monitored conditions are in a state of "Acceptable Status", control system 48 enables operation of x-ray source 40 for generating x-ray energy to create an exposure.

Returning to FIG. 1, control system 48 includes system host display 72 supported by body 26 of base assembly 22 in static, fixed relation thereto. System host display 72 is operable to display a visual representation (not shown) of an indicated state of each monitored condition. In the specific embodiment illustrated, system host display 72 is operable to display for each condition a visual representation in the alternative states of "Inhibit Status" and "Acceptable Status". In the specific arrangement illustrated, system host display 72 is operable to display for each condition a visual representation of the respective condition which is a first color in the "Inhibit Status" state and a second color in the "Acceptable Status" state. Thus, in the specific embodiment illustrated, the first color, red, is displayed indicating "Inhibit Status" and the second color, green, is displayed indicating "Acceptable Status". One skilled in the art will appreciate that, in other embodiments (not shown), system host display 72 is operable in any suitable manner to display a visual representation of an indicated state of each monitored condition. As described in the preceding, in the specific embodiment illustrated, system host display 72 is adapted to display each condition wherein the indicated state is "Inhibit Status". In will be further appreciated by those skilled in the art that system host display 72 can include at least one data entry device (not shown), such as a keypad, mouse, scroll wheel or touchpad, suitable for operator 18 to enter data into and interact with control system 48.

Control system 48 includes portable visual indicator 74 which is independent of base assembly 22 and portable in relation thereto. Portable visual indicator 74 is adapted to be carried by operator 18 when the operator 18 is moving about in remote relation to fixed system host display 72 and base assembly 22. In the specific embodiment illustrated, it can be observed by reference to FIG. 1 that portable visual indicator 74 is manually portable by operator 18 in relation to system host display 72 and base assembly 22. It will be appreciated by those skilled in the art that portable visual indicator 74 can be carried by operator 18 in any suitable manner. In certain embodiments (not shown), portable visual indicator 74 is carried by operator 18 by being clipped on a belt clip or lanyard. Portable visual indicator 74 carried by operator 18 thus is portable in relation to system host display 72, base assembly 22, foldable arm 36, subject 14 and the surrounding environment. Portable visual indicator 74 is carried as operator 18 moves about to make adjustments and changes to apparatus 10, subject 14 and the surrounding environment. It will be appreciated by those skilled in the art that, in order for control system 48 to enable operation of x-ray source 40 to generate x-ray energy for creating an exposure, it is necessary for operator 18 to make certain manual changes, allowances and adjustments to apparatus 10, human subject 14 and the surrounding environment as necessary to change to "Acceptable Status" all conditions which are indicated to be in a state of "Inhibit Status". It will also be appreciated by those skilled in the art that operator 18 can, when desired, momentarily set aside portable visual indicator 74, make such changes, allowances and adjustments, and then retrieve the portable visual indicator 74.

Figure 3:
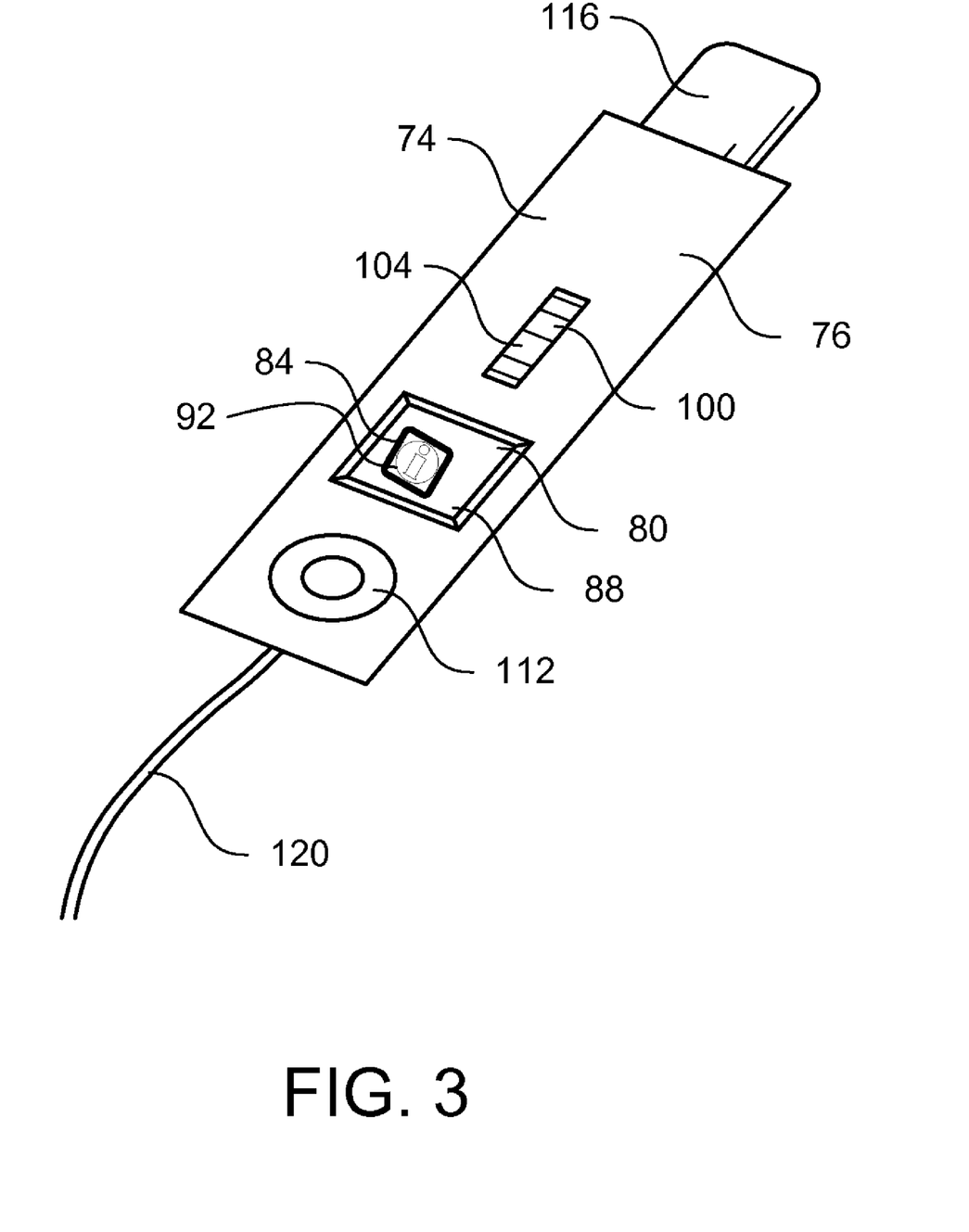
FIG. 3 is an enlarged top view of the portable visual indicator shown generally in FIG. 1.

FIG. 3 is an enlarged top view of portable visual indicator 74 shown generally in FIG. 1. Portable visual indicator 74 includes portable housing 76. Portable housing 76 houses and supports a portable visual display 80. Portable visual display 80 is adapted for selective visual display to operator 18 (see FIG. 1) of a visual representation 84 of an indicated state of a monitored condition. In the specific embodiment illustrated, portable visual display 80 is an LCD screen 88. In other embodiments, portable visual display 80 can be any visual display (not shown), such as a pixel matrix or LED matrix, suitable to display visual representation 84 for viewing by operator 18. In the illustrated embodiment, visual representation 84 includes a plurality of unique icons 92 displayed individually on LCD screen 88. In the specific embodiment illustrated in FIG. 3, each icon 92 is selectively and individually displayed on LCD screen 88. It is to be understood that, in other specific embodiments (not shown), any desired number of icons 92 can be simultaneously displayed. In an embodiment, each icon 92 represents a respective monitored condition. In the specific embodiment illustrated, control system 48 includes a plurality of unique graphical icons 92 each associated with and identifying a respective monitored condition which is presently in the indicated state of "Inhibit Status". One skilled in the art will appreciate that visual representation 84 can include any visual symbol suitable to identify a respective condition in the state "Inhibit Status" such as, for example, text, an alpha-numeric series, a graphical representation, or any suitable visual symbol. In one specific embodiment, portable visual indicator 74 includes a software application (not shown) which is a display driver stored in suitable memory or storage (not shown) and executable by a suitable processor (not shown) connected to drive operation of LCD screen 88 or other visual display (not shown).

Portable visual indicator 74 includes a manual icon selection mechanism 100 supported by the portable housing 76 and operably connected to portable visual display 80 for selectively causing to be displayed thereon an icon 92 representing a monitored condition. It will be apparent to one skilled in the art that any suitable manual icon selection mechanism 100 can be used. In the specific embodiment illustrated, the manual icon selection mechanism 100 is a scroll wheel 104. Scroll wheel 104 when rotated causes different icons 92 to be selectively and individually displayed on LCD screen 88. It will be appreciated by those skilled in the art that scroll wheel 104 can include a suitable software application stored in memory and executable by a suitable processor to drive operation thereof. Each displayed icon 92 is a visual representation of a respective monitored condition presently in the indicated state of "Inhibit Status". When control system 48 is in "Acquire Mode", each displayed icon 92 provides visual indication to operator 18 that the respective condition is presently in a state of "Inhibit Status". Each displayed icon 92 thus indicates to operator 18 that the respective condition must change from the indicated state of "Inhibit Status" to "Acceptable Status" before control system 48 will enable operation of x-ray source 40 to generate x-ray energy for creating an exposure of subject 14. For example, in a specific embodiment wherein one monitored condition is the temperature of x-ray source 40, when the present temperature of x-ray source 40 exceeds an established operating temperature range and thus is in a state of "Inhibit Status", a respective unique icon 92 representing temperature of x-ray source 40 is displayed and thus indicates to operator 18 that the temperature of x-ray source 40 is in a state of "Inhibit Status". The displayed icon 92 thus indicates to operator 18 that x-ray source 40 presently is too hot for operation to generate x-ray energy and thus must be returned to the established temperature range before control system 48 will enable x-ray source 40 to be operated for generating x-ray energy to create an exposure. Also, for example, in a specific embodiment wherein one monitored condition is distance of subject 14 from x-ray source 40, when the present distance of subject 14 is less than an established minimum acceptable distance for operation and thus is in a state of "Inhibit Status", a respective unique icon 92 representing distance of subject 14 from x-ray source 40 is displayed and thus indicates to operator 18 that the distance of subject 14 from x-ray source 40 is in a state of "Inhibit Status". The displayed icon 92 thus indicates to operator 18 that distance of subject 14 from x-ray source 40 presently is less than the established minimum operating distance and must be increased to the established minimum acceptable distance for operation before control system 48 will enable x-ray source 40 to be operated for generating x-ray energy to create an exposure. Alternatively, for example, in a specific embodiment wherein one monitored condition is distance of the nearest metallic object in the surrounding environment from x-ray source 40, when the present distance of a metallic object closest to x-ray source 40 is less than an established minimum acceptable distance for operation and, thus, the monitored condition is in a state of "Inhibit Status", a respective unique icon 92 representing distance of the nearest metallic object from x-ray source 40 is displayed and thus indicates to operator 18 that the distance of nearest metallic object 14 from x-ray source 40. The displayed icon 92 thus indicates to operator 18 that distance of the nearest metallic object from x-ray source 40 is less than the established minimum acceptable distance for operation and, thus, the monitored condition is in a state of "Inhibit Status". The displayed icon 92 thus indicates to operator 18 that distance of nearest object 14 from x-ray source 40 presently is less than the established minimum operating distance and must be increased to the established minimum acceptable distance for operation before control system 48 will enable x-ray source 40 to be operated for generating x-ray energy to create an exposure of subject 14. It will also be appreciated by those skilled in the art that, in embodiments (not shown) a plurality of icons 92 can be displayed simultaneously on LCD screen 88. It is to be understood that, in embodiments, each icon 92 is a visual representation produced by execution of a suitable software application.

Portable visual indicator 74 includes an Enabled/Disabled visual indicator 112 supported by portable housing 76 and connected to indicate to operator 18 that control system 48 has enabled operation of x-ray source 40 to be operated to generate x-ray energy for creating an exposure. When the indicated states of all monitored conditions are "Acceptable Status", the Enabled/Disabled visual indicator 112 indicates to operator 18 that control system 48 has enabled x-ray source 40 to be operated to generate x-ray energy for creating an exposure of subject 14. The x-ray source 40, thus enabled by control system 48, is caused to operate to generate x-ray energy by manual operation of exposure prep and hold switch 116 by operator 18 as further described herein. Conversely, when the indicated state of at least one monitored condition is "Inhibit Status", the Enabled/Disabled visual indicator 112 indicates to the operator 18 that control system 48 has disabled x-ray source 40 from being operated to generate x-ray energy for creating an exposure. The x-ray source 40 when disabled by control system 48 is not caused to operate by manual operation of the exposure prep and hold switch 116. One skilled in the art will appreciate that the Enabled/Disabled visual indicator 112 can be of any construction suitable to provide to operator 18 visual indication when control system 48 has enabled operation of x-ray source 40 and, alternatively, when control system 48 has disabled operation of x-ray source 40. In the specific embodiment illustrated, the Enabled/Disabled visual indicator 112 is a light which is illuminated in the color green when control system 48 has enabled operation of x-ray source 40 and, alternatively, in the color red when control system 48 has disabled operation of x-ray source 40.

Portable visual indicator 74 includes exposure prep and hold switch 116 supported by portable housing 76 and connected for selectively operating x-ray source 40 to generate x-ray energy. Any exposure prep and hold switch 116 suitable for selective operation of x-ray source 40 can be used. In the specific embodiment illustrated, exposure prep and hold switch 116 is a two stage button-type switch 120. Exposure prep and hold switch 120 includes a button which is biased, such as by a spring loaded return, to an open or initial stage "off" position. Exposure prep and hold switch 120 is selectively movable from the initial stage "off" position to an intermediate or first stage "prep" position by being depressed. Exposure prep and hold switch 120 is selectively movable from the first stage "prep" position to a final or second stage "operating" position by being further depressed. One skilled in the art will appreciate that exposure prep and hold switch 116 is connected such that, when the Enabled/Disabled visual indicator light 112 indicates that operation of x-ray source 40 is enabled by control system 48, the operator 18 selectively depressing the button thereof from the initial stage "off" position to the first stage "prep" position and then to the second stage "operating" position operates x-ray source 40 to generate x-ray energy for creating an exposure image of subject 14.

Control system 48 includes communications link or remote connection 120 operable to provide communication between portable visual indicator 74 and control system elements housed in base assembly 22. In the specific embodiment illustrated in FIG. 1, remote connection 120 is a flexible, hardwired connection 124 extending between portable housing 76 and base assembly 22 to provide communication of signals between respective elements of control system 48. In the specific embodiment illustrated in FIG. 1 and FIG. 2, flexible hardwired connection 124 includes cable 126. One skilled in the art will appreciate that hardwired connection 124 can be formed in any suitable manner. In the specific embodiment illustrated, cable 126 is of suitable construction to provide bidirectional communication of signals between elements of control system 48 supported by portable housing 76 and elements of control system 48 supported by base assembly 22. In other embodiments (not shown), cable 126 is of suitable construction to provide unidirectional communication of signals.

Figure 4:
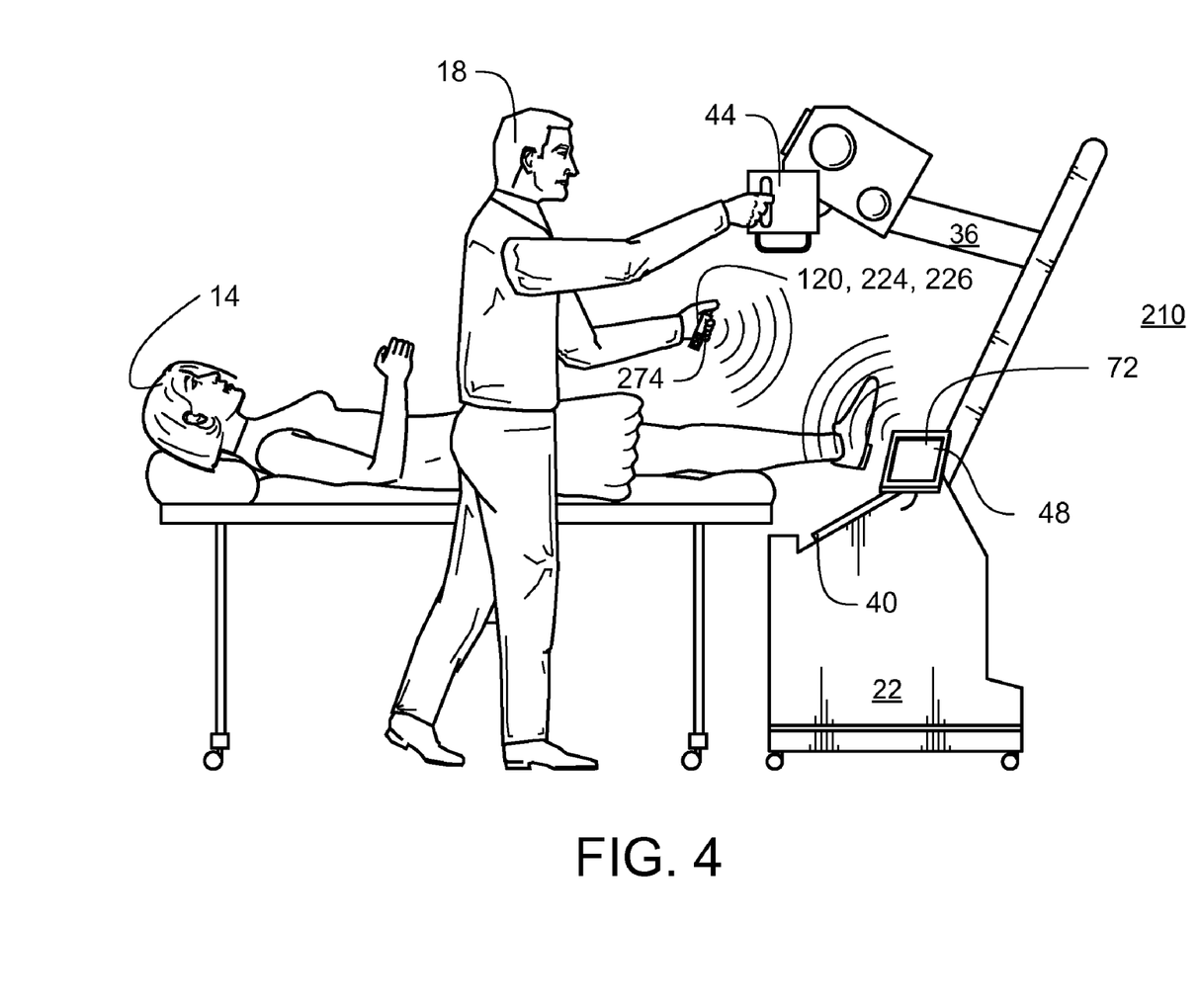
FIG. 4 is a side view of an x-ray apparatus according to a second embodiment.

FIG. 4 is a side view of an x-ray apparatus 210 according to a second embodiment. X-ray apparatus 210 is identical to previously described x-ray apparatus 10, except as otherwise described herein. In the specific embodiment illustrated in FIG. 4, remote connection 120 includes wireless communication link or wireless connection 224. Wireless connection 224 is operable to provide communication between portable visual indicator 274 and control system elements housed in base assembly 22. In the specific embodiment illustrated in FIG. 4, wireless connection 224 includes an 802.11(g) wireless protocol connection 226 which provides bidirectional communication of signals between respective 802.11(g) wireless communication chipsets (not shown) in portable visual indicator 274 and base assembly 22. In the specific embodiment illustrated, wireless connection 224 including 802.11(g) wireless protocol connection 226 is adapted to provide bidirectional communication of signals between elements of control system 48 of portable visual indicator 274 and elements of control system 48 supported by base assembly 22. It is to be understood that wireless connection 224 can be of different construction suitable to provide the function of remote wireless communication. For example, in different specific embodiments, wireless connection 224 can be a suitable 802.11(c), infrared, wi-fi, wi-max, cellular or other suitable wireless communication connection between portable visual indicator 274 and base assembly 22.

Figure 5:
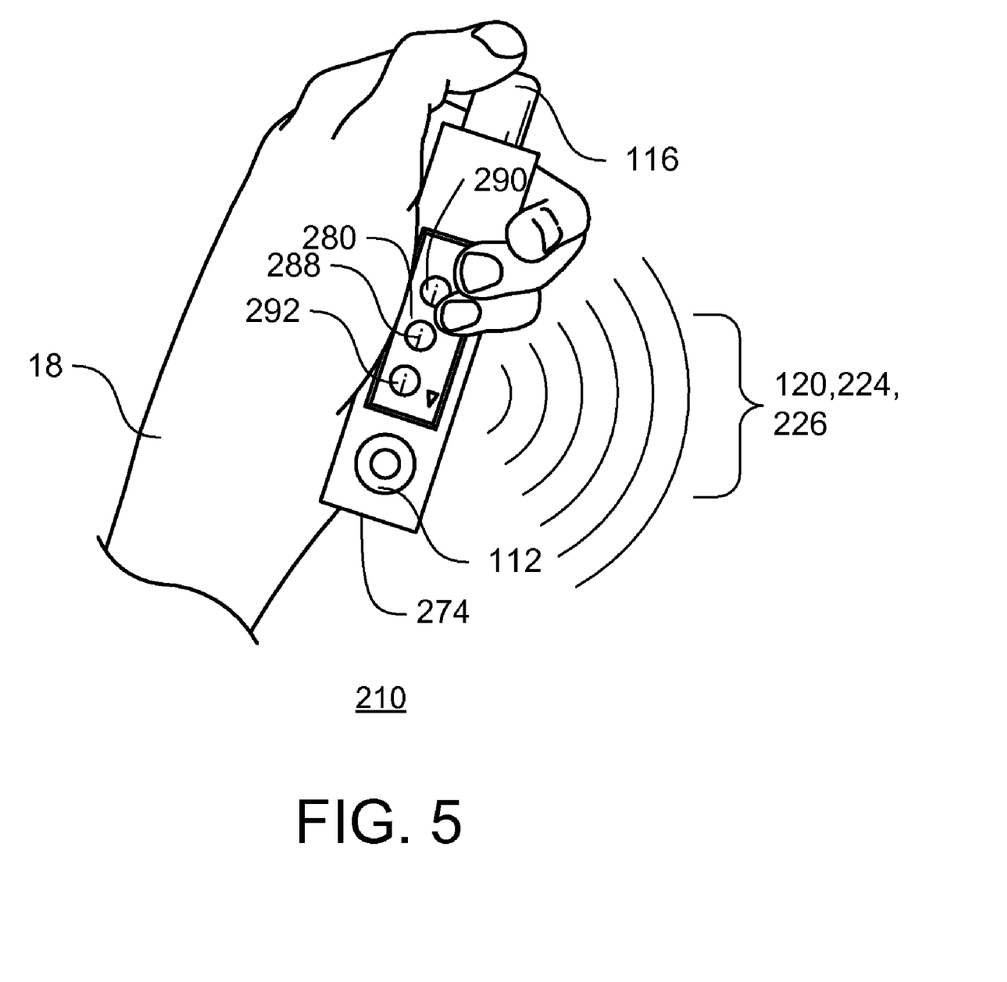
FIG. 5 is an enlarged top view of the portable visual indicator shown generally in FIG. 4.

FIG. 5 is an enlarged top view of the portable visual indicator 274 shown generally in FIG. 4. Portable visual indicator 274 is identical to portable visual indicator 74 previously described in connection with x-ray apparatus 10, except as otherwise described herein. Portable visual indicator 274 includes portable visual display 280. Portable visual display 280 includes touch screen display 284. Touch screen display 284 includes displayed icon 288 indicating the state of a monitored condition, as previously described. Touch screen display 284 includes a pair of input buttons 290, 292. Input buttons 290, 292 are suitable for inputting data, such as by scrolling through a plurality of displayed icons 288 and, alternatively, for entering data and changing information by incrementing up and down using respective input buttons 290, 292.

Conclusion

Embodiments improve the capability of operator 18 to immediately view the portable visual indicator and determine readiness of x-ray apparatus 10 for making an exposure. Embodiments improve visual coverage or visibility of portable visual indicator 74 and related feedback to operator 18. Embodiments reduce demand for time and foot travel of operator 18 to repeatedly return to system host display 72, and thus provide increased opportunity for operator 18 to quickly and efficiently position x-ray apparatus 10, subject 14, film and the surrounding environment and reduce time required to take an exposure, with confidence that control system 48 will not disable operation of x-ray source 40. Embodiments provide visual information in close proximity to operator 18 and thus reduce visibility requirements for information displayed on the more distant system host display 72. Embodiments provide the display of desired information, such as technique settings and the subject name, to operator 18 via portable visual indicator 74.

X-ray apparatus is described. Although specific embodiments are illustrated and described herein, it will be appreciated by those of ordinary skill in the art that any arrangement which is calculated to achieve the same purpose may be substituted for the specific embodiments shown. This application is intended to cover any adaptations or variations. One of ordinary skill in the art will appreciate that implementations can be made for other embodiments that provide the required function. In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. The terminology used in this application is meant to include all environments and alternate technologies which provide the same functionality as described herein.

I claim:

1. X-ray apparatus for imaging a subject, the X-ray apparatus having a base assembly and an X-ray source supported by the base assembly, the X-ray source being operable for generating X-ray energy, the X-ray apparatus having a control system for controlling operation of the X-ray source, the X-ray apparatus comprising:

a plurality of detectors, each detector operable to detect a respective monitored condition and operable to generate detector output; the control system receiving the detector output; and the control system including a portable visual indicator independent of the base assembly and portable in relation thereto, the portable visual indicator displaying a state of the monitored condition wherein the monitored condition includes all of the following: apparatus conditions, subject conditions, environment conditions, procedure information and subject information.

2. X-ray apparatus according to claim 1 and comprising:
the portable visual indicator being manually carried by the operator.

3. X-ray apparatus according to claim 1 and comprising:
the portable visual indicator includes a display driver stored in a memory and executable by a suitable processor connected to drive operation of a LCD visual display.

4. X-ray apparatus according to claim 1 and comprising:
the control system including a visual representation displayed on the portable visual indicator, the visual representation indicating the state of the monitored condition.

5. X-ray apparatus according to claim 1 and comprising:
the control system including a control for selectively displaying different visual representations from among a plurality of the same.

6. X-ray apparatus according to claim 1 and comprising:
the control system including an exposure prep and hold switch selectively operable by the operator for initiating operation of the X-ray source, the exposure prep and hold switch being supported by the portable visual indicator.

7. X-ray apparatus according to claim 1 and comprising:
the control system including a remote connection operable to provide communication between the portable visual indicator and the base assembly.

8. X-ray apparatus according to claim 7 and comprising:
the remote connection including a flexible hardwired cable connected between the portable visual indicator and the base assembly.

9. X-ray apparatus according to claim 7 and comprising:
the remote connection including a wireless connection operable to provide communication between elements of the control system supported by the portable visual indicator and elements of the control system supported by the base assembly.

10. An X-ray apparatus having a base assembly, the X-ray apparatus comprising:
a control system including a portable visual indicator carried by an operator and portable in relation to the base assembly, the portable visual indicator having a portable visual display;
the control system including a visual representation of at least one condition displayed on the portable visual display wherein the at least one condition includes all of the following: apparatus conditions, subject conditions, environment conditions, procedure information and subject information; and
the control system including a control for selectively displaying different visual representations from among a plurality of the same, wherein the different visual representations are graphical icons each associated with and identifying a respective condition of the at least one condition.

11. The Xray apparatus according to claim 10, wherein the portable visual indicator further comprises a manual icon selection mechanism.

12. The X-ray apparatus according to claim 10 and comprising:
the visual representation indicating a state of the at least one condition.

13. The X-ray apparatus according to claim 10, wherein each of the icons are displayed simultaneously on the visual display.

14. The X-ray apparatus according to claim 10 and comprising:
the control system including an exposure prep and hold switch selectively operable by the operator for initiating operation of an X-ray source, the exposure prep and hold switch being supported by the portable visual indicator.

15. The X-ray apparatus according to claim 10 and comprising:
the control system including a remote connection operable to provide communication between the portable visual indicator and the base assembly.

16. The X-ray apparatus according to claim 15 and comprising:
the remote connection including a flexible hardwired cable connected between the portable visual indicator and the base assembly.

17. The X-ray apparatus according to claim 15 and comprising:
the remote connection including a wireless connection operable to provide communication between elements of the control system supported by the portable visual indicator and elements of the control system supported by the base assembly.

18. An X-ray apparatus for imaging a subject, the X-ray apparatus having a base assembly and an X-ray source supported by the base assembly, the X-ray source being operable for generating X-ray energy, the X-ray apparatus having a control system for controlling operation of the X-ray source the X-ray apparatus including a plurality of detectors, each detector being operable to monitor a respective condition; the X-ray apparatus comprising:
the control system including a portable visual indicator carried by an operator, the portable visual indicator having a portable visual display, the control system including a plurality of visual representations, each visual representation corresponding to a respective condition, the condition including all of the following apparatus conditions, subject conditions, environment conditions, procedure information and subject information, the portable visual indicator including at least one of the visual representations displayed on the portable visual display, the at least one of the visual representations indicating a state of the respective at least one condition; and the control system including a control for selectively displaying different visual representations from among the plurality of visual representations, wherein the different visual representations are graphical icons each associated with and identifying a respective condition of the at least one condition.

19. The X-ray apparatus according to claim 18 wherein the control system includes an exposure prep and hold switch selectively operable by the operator for initiating operation of the X-ray source, the exposure prep and hold switch being supported by the portable visual indicator.

20. The X-ray apparatus according to claim 18 and comprising:
the control system including a remote connection operable to provide communication between a portable housing of the portable visual display and the base assembly.

* * * * *

UNITED STATES PATENT AND TRADEMARK OFFICE
Certificate

Patent No. 7,502,444 B2                                Patented: March 10, 2009

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Rajeev R. Marar, Waukesha, WI (US); and Kevin Andrew Coombs, Pewaukee, WI (US).

Signed and Sealed this Fourteenth Day of August 2012.

MINH-TOAN TON
*Supervisory Patent Examiner*
Art Unit 2882
Technology Center 2800